(12) United States Patent
Kim et al.

(10) Patent No.: US 8,409,621 B2
(45) Date of Patent: *Apr. 2, 2013

(54) MICROPARTICLES

(75) Inventors: Kyekyoon Kim, Champaign, IL (US);
Hyungsoo Choi, Champaign, IL (US);
Young Bin Choy, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 664 days.

This patent is subject to a terminal disclaimer.

(21) Appl. No.: 11/939,262

(22) Filed: Nov. 13, 2007

(65) Prior Publication Data

US 2008/0181964 A1   Jul. 31, 2008

Related U.S. Application Data

(63) Continuation of application No. 10/728,190, filed on Dec. 4, 2003, now Pat. No. 7,309,500.

(51) Int. Cl.
| | | |
|---|---|---|
| *A61K 9/14* | (2006.01) | |
| *A61K 47/30* | (2006.01) | |
| *A61K 47/38* | (2006.01) | |
| *A61K 9/16* | (2006.01) | |
| *A61K 9/50* | (2006.01) | |
| *B29B 9/00* | (2006.01) | |

(52) U.S. Cl. ........ 424/497; 424/489; 424/501; 424/490; 424/491; 424/492; 424/494; 424/495; 514/772.4; 514/772.5; 514/781; 514/777; 514/779; 264/9

(58) Field of Classification Search .................. 424/489, 424/490, 491, 492, 494, 495, 497, 501; 514/772.4, 514/772.5, 781, 777, 779; 264/9
See application file for complete search history.

(56) References Cited

U.S. PATENT DOCUMENTS

| | | |
|---|---|---|
| 3,579,245 A | 5/1971 | Berry |
| 4,356,528 A | 10/1982 | Coffee |
| 4,444,961 A | 4/1984 | Timm |
| 4,748,043 A | 5/1988 | Seaver et al. |
| 4,861,627 A | 8/1989 | Mathiowitz et al. |
| 5,019,400 A | 5/1991 | Gombotz et al. |
| 5,260,002 A | 11/1993 | Wang |
| 5,340,090 A | 8/1994 | Orme et al. |
| 5,344,676 A | 9/1994 | Kim et al. |
| 5,445,666 A | 8/1995 | Peschka et al. |
| 5,462,866 A | 10/1995 | Wang |

(Continued)

FOREIGN PATENT DOCUMENTS

| | | |
|---|---|---|
| CA | 2419115 | 2/2002 |
| CH | 675 370 A5 | 9/1990 |

(Continued)

OTHER PUBLICATIONS

"Preparation of monodisperse controlled release microcapsules", Brandau, International Journal of Pharmaceutics, 242 (2002), p. 179-184.*

(Continued)

*Primary Examiner* — Ernst Arnold
*Assistant Examiner* — Hong Yu
(74) *Attorney, Agent, or Firm* — Guntin & Gust, PLC; Ed Guntin

(57) ABSTRACT

A method of forming particles, comprises accelerating a first stream comprising a first liquid, applying a charging voltage of at most 1.5 kV to the first stream, and vibrating the first stream, to form particles.

32 Claims, 8 Drawing Sheets

U.S. PATENT DOCUMENTS

| | | | |
|---|---|---|---|
| 5,585,020 A * | 12/1996 | Becker et al. | 219/121.85 |
| 5,650,173 A | 7/1997 | Ramstack et al. | |
| 5,654,008 A | 8/1997 | Herbert et al. | |
| 5,667,808 A | 9/1997 | Johnson et al. | |
| 5,674,534 A | 10/1997 | Zale et al. | |
| 5,711,968 A | 1/1998 | Tracy et al. | |
| 5,716,644 A | 2/1998 | Zate et al. | |
| 5,792,477 A | 8/1998 | Rickey et al. | |
| 5,817,343 A | 10/1998 | Burke | |
| 5,874,111 A | 2/1999 | Maitra et al. | |
| 5,891,478 A | 4/1999 | Johnson et al. | |
| 5,912,015 A | 6/1999 | Bernstein et al. | |
| 5,916,597 A | 6/1999 | Lee et al. | |
| 5,916,598 A | 6/1999 | Rickey et al. | |
| 5,922,253 A | 7/1999 | Herbert et al. | |
| 5,948,483 A | 9/1999 | Kim et al. | |
| 5,954,907 A | 9/1999 | LaRose et al. | |
| 5,985,354 A | 11/1999 | Mathiowitz et al. | |
| 5,989,463 A | 11/1999 | Tracy et al. | |
| 6,051,259 A | 4/2000 | Johnson et al. | |
| 6,060,128 A | 5/2000 | Kim et al. | |
| 6,110,503 A | 8/2000 | Rickey et al. | |
| 6,110,921 A | 8/2000 | Mesens et al. | |
| 6,116,516 A | 9/2000 | Ganan-Calvo | |
| 6,119,953 A | 9/2000 | Ganan-Calvo et al. | |
| 6,153,129 A | 11/2000 | Herbert et al. | |
| 6,174,469 B1 | 1/2001 | Ganan-Calvo | |
| 6,183,781 B1 | 2/2001 | Burke | |
| 6,187,214 B1 | 2/2001 | Ganan-Calvo | |
| 6,189,803 B1 | 2/2001 | Ganan-Calvo | |
| 6,194,006 B1 | 2/2001 | Lyons et al. | |
| 6,196,525 B1 | 3/2001 | Ganan-Calvo | |
| 6,197,835 B1 | 3/2001 | Ganan-Calvo | |
| 6,224,794 B1 | 5/2001 | Amsden et al. | |
| 6,302,331 B1 | 10/2001 | Dvorsky et al. | |
| 6,447,752 B2 | 9/2002 | Edwards et al. | |
| 6,447,753 B2 | 9/2002 | Edwards et al. | |
| 6,458,296 B1 | 10/2002 | Heinzen et al. | |
| 6,458,387 B1 | 10/2002 | Scott et al. | |
| 6,669,961 B2 | 12/2003 | Kim et al. | |
| 7,309,500 B2 * | 12/2007 | Kim et al. | 424/489 |
| 7,368,130 B2 | 5/2008 | Kim et al. | |
| 2002/0054912 A1 * | 5/2002 | Kim et al. | 424/489 |
| 2002/0160109 A1 | 10/2002 | Yeo et al. | |
| 2004/0022939 A1 | 2/2004 | Kim et al. | |
| 2004/0079360 A1 | 4/2004 | Coffee et al. | |
| 2005/0123614 A1 | 6/2005 | Kim et al. | |
| 2006/0110544 A1 | 5/2006 | Kim et al. | |
| 2008/0175915 A1 | 7/2008 | Kim et al. | |

FOREIGN PATENT DOCUMENTS

| | | |
|---|---|---|
| DE | 27 25 849 A1 | 12/1978 |
| EP | 0 258 016 A | 3/1988 |
| EP | 0 265 924 A2 | 4/1988 |
| WO | WO 97/31691 | 4/1997 |
| WO | WO 98/58745 | 12/1998 |
| WO | WO 99/44735 | 10/1999 |
| WO | WO 02/13786 | 2/2002 |
| WO | WO 2006/057766 A1 | 6/2006 |
| WO | WO 2005/055988 | 8/2006 |

OTHER PUBLICATIONS

"Electrostatic spraying and its use in drug delivery-cholestrol microsphere" Reyderman et al., International Journal of Pharmaceutics, 124 (1995), p. 75-85.*

Aldrich, "Microparticle Size Standards," Aldrich Technical Bulletin, AL-203, pp. 1-2, 1997.

Amsden, B., "The production of uniformly sized polymer microspheres," Pharm. Res. 16, 1140-1143, 1999.

Amsden, B.G. et al., "An examination of factors affecting the size, distribution, and release characteristics of polymer microbeads made using electrostatics," J. Controlled Rel. 43, 183-196, 1997.

Banerjee, T., et al., "Preparation, characterization and biodistribution of ultrafine chitosan nanoparticles," Int. J. Pharm. 243, 93-105, 2002.

Berkland, C. et al., "Fabrication of PLG microspheres with precisely controlled and monodisperse size distributions," Journal of Controlled Release, vol. 73, pp. 59-74, May 18, 2001.

Berkland, C., et al., "Precise control of PLG microsphere size provides enhanced control of drug release rate," Journal of Controlled Release, vol. 82. pp. 137-147, 2002.

Berkland, et al., "Controlled Release from Uniform Two-Polymer Microcapsules", Proceedings of the International Symposium on Controlled Release of Bioactive Materials, vol. 30, pp. 350, (2003).

Bittner, B. et al., "Ultrasonic Atomization for Spray Drying: A Versatile Technique for the Preparation of Protein Loaded Biodegradable Microspheres," Journal of Microencapsulation, vol. 16:3, p. 325-341, 1999.

Brandau, T., "Preparation of monodisperse controlled release microcapsules," Int. J. Pharm. 242: 179-184, 2002.

Crotts, G. et al., "Preparation of porous and nonporous beiodegradable polymeric hollow microspheres," J. Controlled Rel. 35, 91-105, 1995.

Foster, C.A., et al., "Apparatus for producing uniform solid spheres of hydrogen," Rev. Sci. Instrum., vol. 48, No. 6, pp. 625-631, 1977.

Gilliard, R.P., et al., "Spherical hydrogen pellet generator for magnetic confinement fusion research," Rev. Sci. Instrum., vol. 52, No. 2, pp. 183-190, 1981.

Guttman, C.D. et al., "An investigation of the effects of system parameters on the production of hollow hydrogen droplets," J. Appl. Phys., vol. 50, No. 6, pp. 4139-4142, Jun. 1979.

He, P., et al., "Chitosan microspheres prepared by spray drying," Int. J. Pharm. 187, 53-65, 1999.

Hendricks, C.D., et at., "Interaction of a stream of dielectric spheres in an electric field in a high vacuum," IEEE Trans. Ind. Appl., vol. Ia-21, No. 3, pp. 705-708, 1985.

Huang, Y., et al., "Formulation factors in preparing BTM-chitosan microspheres by spray drying method," Int. J. Pharm. 242, 239-242, 2002.

International Search Report dated Mar. 16, 2006 for PCT application No. PCT/US2004/040195.

Jang, K.Y. et al., "Evaluation of sol-gel processing as a method for fabricating spherical-shell silica aerogel ICF targets," J. Vac. Technol. A, vol. 10, No. 4, pp. 1152-1157, 1992.

Jang, K.Y. et al., "Study of sol-gel processing for fabrication of hollow silica-aerogel spheres," J. Vac. Sci. Technol. A, 8:3, pp. 1732-1735, 1990.

Kim, K. et al., "Generation of charged drops of insulating liquids by electrostatic spraying," J. Appl. Phys., vol. 47, No. 5, pp. 1964-1969, May 1976.

Kim, K. et al., "Hollow silica spheres of controlled size and porosity by sol-gel processing," J. Am. Ceram. Soc., 74:8, pp. 1987-1992, 1991.

Kim, K., "Fabrication of glass micro- and nanospheres from liquid precursors using droplet generation and sot-gel processing," Mat. Res. Soc. Symp. Proc., vol. 372, pp. 25-32, 1995.

Kim, K., et al., "Fabrication of hollow silica aerogel spheres by a droplet generation method and sol-gel processing," J. Vac. Sci, Technol. A., vol. 7, No. 3, pp. 1181-1184, 1989.

Kirwan, J.E., et at., "An experimental and theoretical study of a monodisperse spray," AIAA J. Propulsion and Power, vol. 4, No. 4, pp. 299-307, 1988.

Ko, J., et al., "Preparation and characterization of chitosan microparticles intended for controlled drug delivery," Int. J. Pharm. 249, 165-174, 2002.

Koizumi, Makoto, et al., "Allosteric selection of ribozymes that respond to the second messengers cGMP and cAMP," Nature Structural Biology, vol. 6, pp. 1062-1071, 1999.

Leach, K.J., et al., "Degradation of double-walled polymer microspheres of PLLA and P(CPP:SA) 20:80. I. In vitro degradation," 1973-1980, 1998.

Leach, K.L., et al., "Degradation of double-walled polymer microspheres of PLLA and P(CPP:SA) 20:80 II in vivo degradation," Biomaterials, 19:1981-1988, 1998.

Lee, T.H., et al., "Double-walled microspheres for the sustained release of a highly water soluble drug: characterization and irradiation studies," J. Controlled Release, 83:437-452, 2002.

Leelarasamee, N. et al., "A method for the preparation of polylactic acid microcapsules of controlled particle size and drug loading," Journal of Microencapsulation 5, 147-157, 1988.

Loscertales, I.G., et al., Micro-nano encapsulation via electrified coaxial liquid jets, Science, 295, pp. 1695-1698, (2002).

Mok, L.S. et al., "Equilibrium of a liquid in a spherical shell due to gravity, surface tension, and van der Walls forces," Phys. Fluids, vol. 28, No. 5, pp. 1227-1232, May 1985.

Reyderman, L. et al., "Electrostatic spraying and its use in drug delivery—cholesterol microspheres," Int. J. Pharm. 124, 75-85, 1995.

Sanchez, A. et al., "Pulsed controlled-release system for potential use in vaccine delivery," Pharm. Sci. 85, 547-552, 1996.

Sansdrap, P. et al., "Influence of manufacturing parameters on the size characteristics and the release profiles of nifedipine from poly(DL-lactide-co-glycolide) microspheres," Int. J. Pharm. 98, 157-164, 1993.

Santoro, Stephen, et al., "A general purpose RNA-cleaving DNA enzymes," Proceedings of National Academy of Science, vol. 94, pp. 4262-4266, 1997.

Shi, M., al., M. et al "Double walled POE/PLGA microspheres: encapsulation of water-soluble and water-insoluble proteins and their release properties," J. Controlled Release, 89:167-177, 2003.

Shiga, K. N. Muramatsu et al., "Preparation of poly(D,L-lactide) and copoly(lactide-glycolide) microspheres of uniform size," J. Pharm,. Pharmacol 48, 891-895, 1996.

Skoog, D., et al., from Fundamentals of Analytical Chemistry, fourth edition, Section 3C-2, 51-53, 1982.

Tracy, M.A., "Development and scale-up of a microsphere protein delivery system," Biotechnol. Prog. 14, 108-115, 1998.

Yang, Y., et al., "POE/PLGA composite microspheres: formation and in vitro behavior of double walled microspheres," J. Controlled Release 88:201-213, 2003.

You, J. et al., "Preparation of regular sized ca-alginate microspheres using membrane emulsification method," Journal of Microencapsulation, vol. 18, No. 4, pp. 521-532, 2001.

International Search Report dated Jan. 30, 2003 for PCT application No. PCT/US2001/25674.

Utada, A.S., et al., "Monodisperse double emulsions generated from a microcapillary device", Science, vol. 308, pp. 537-541, (2005).

Groenendaal, L., et al., "Poly(3,4-ethylenedioxythiophene) and its derivatives: Past, Present, and Future", Advanced Materials, vol. 12, No. 7, pp. 481-494, (2000).

Schrauwers, A., "Focused spraying: Fighting plant disease without making a mess", Delft Outlook, pp. 1, 6-16, located at http://www.delftoutlook.tudelft.nl/info/index.cfm?hoofdstuk=article&ArtID=5558, (2003).

International Search Report dated Apr. 6, 2006 for PCT application No. PCT/US2005/038995.

Berkland, C., et al., "Fabrication of PLG microspheres with precisely controlled and monodisperse size distributions"., Journal of Controlled Release, vol. 73, pp. 59-74, (2001).

International Search Report dated Mar. 16, 2006 for corresponding PCT application No. PCT/US2004/040195.

You, J.-O., et al., "Preparation of regular sized Ca-alginate microspheres using membrane emulsification method"., Journal of Microencapsulation, vol. 18, No. 4, pp. 521-532, (2001).

Ko, J., et al., "Preparation and characterization of chitosan microparticles intended for controlled drug delivery," Int. J. Pharm. 249, 165-174 (2002).

Banerjee, T., et al., "Preparation, characterization and biodistribution of ultrafine chitosan nanoparticles," Int. J. Pharm. 243, 93-105 (2002).

Huang, Y., et al., "Formulation factors in preparing BTM-chitosan microspheres by spray drying method," Int. J. Pharm. 242, 239-242 (2002).

Berkland, C., et al., "Fabrication of PLG microspheres with precisely controlled and monodisperse size distributions," J. Control. Release 73, 59-74 (2001).

He, P., et al., "Chitosan microspheres prepared by spray drying," Int. J. Pharm. 187, 53-65 (1999).

Berkland, C., et al., "Precise control of PLG microsphere size provides enhanced control of drug release rate," Journal of Controlled Release, vol. 82, pp. 137-147 (2002).

Foster, C.A., et al., "Apparatus for producing uniform solid spheres of hydrogen," Rev. Sci. Instrum., vol. 48, No. 6, pp. 325-631, (1977).

Gilliard, R.P., et al., "Spherical hydrogen pellet generator for magnetic confinement fusion research," Rev. Sci. Instrum., vol. 52, No. 2, pp. 183-190, (1981).

Hendricks, C.D., et al., "Interaction of a stream of dielectric spheres in an electric field in a high vacuum," IEEE Trans. Ind. Appi., vol. Ia-21, No. 3, pp. 705-708 (1985).

Kirwan, J.E., et al., "An experimental and theoretical study of a monodisperse spray," AIAA J. Propulsion and Power, vol. 4, No. 4, pp. 299-307, (1988).

Kim, N.K., et al., "Fabrication of hollow silica aerogel spheres by a droplet generation method and sol-gel processing," J. Vac. Sci, Technol. A., vol. 7, No. 3, pp. 1181-1184, (1989).

Kim, K., "Fabrication of glass micro- and nanospheres from liquid precursors using droplet generation and sol-gel processing," Mat. Res. Soc. Symp. Proc., vol. 372, pp. 25-32 (1995).

Reyderman, L. et al., "Novel methods of microparticulate production: application to drug delivery," Pharm. Dev. Technol, vol. 1, No. 3, pp. 223-229, (1996).

Kim, K. et al., "Generation of charged liquid cluster beam of liquid-mix precursors and application to nanostructured materials", Nanostructured Materials, vol. 4, No. 5, pp. 597-602, (1994).

* cited by examiner

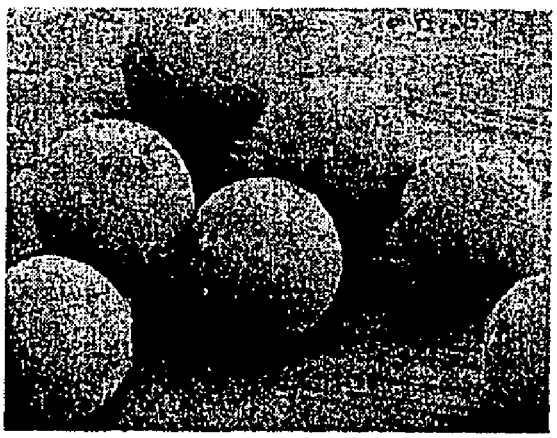 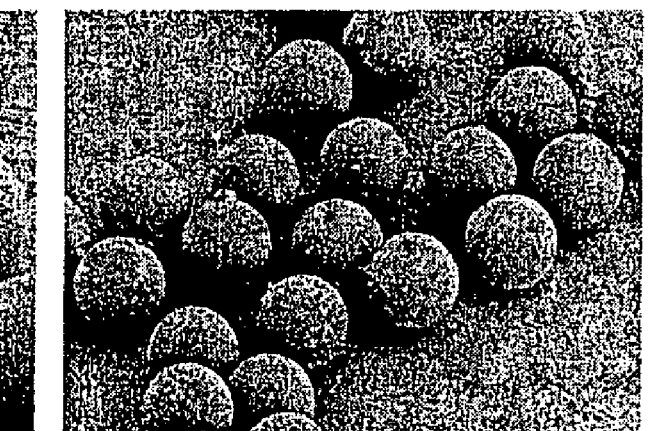
A      Figure 3      B

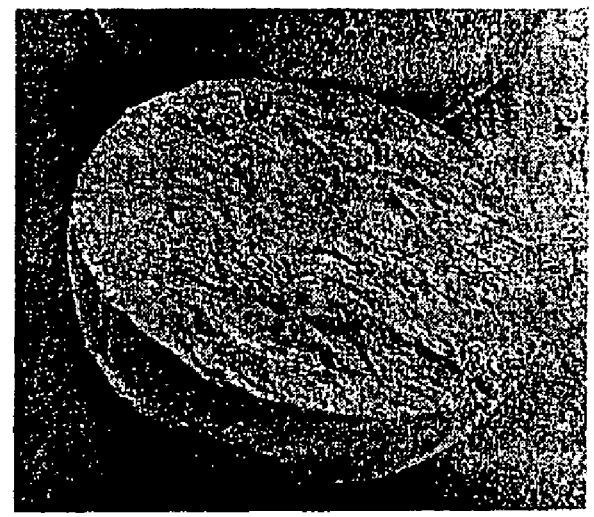
A  Figure 4  B

MICROPARTICLES

CROSS REFERENCE TO RELATED APPLICATION

This application is a continuation application of co-pending application Ser. No. 10/728,190 filed Dec. 4, 2003 now U.S. Pat. No. 7,309,500.

BACKGROUND

Rapid advances in biotechnology have led to the discovery of numerous protein and peptide therapeutics, many of which have recently reached the marketplace or are currently under regulatory review by the United States Food and Drug Administration. Unlike traditional small-molecule drugs, however, proteins and peptides generally cannot be administered orally; injection or infusion is most often required. Further, because of their fragility and short in vivo half-lives, encapsulation of proteins in biodegradable polymeric devices, from which the drug can be delivered, locally or systemically, for a prolonged period of time, has been a promising and intensely studied solution to these problems.

Biodegradable microparticles containing a variety of polymers have been the most studied delivery vehicle due to relatively simple fabrication and facile administration to a variety of locations in vivo through a syringe needle. One particularly preferred microparticle material is chitosan, a hydrophilic biodegradable natural polymer that has been used for drug delivery systems in recent years. To manufacture microparticles of chitosan for this type of application, various methods have been employed, including spray drying and classic emulsions, both at the bench and industrial scales. However, neither technique has yielded uniform microparticles and microcapsules (to be collectively referred to as microparticles) with precisely controlled size and size distribution. In fact, standard deviations equal to 25-50% of the mean diameter are not uncommon.

Control of particle size and size distribution has several important implications for controlled-release drug delivery. For example, there typically is an ideal particle size that provides a desired release rate and route of administration. Microparticles that are "too small" exhibit poor encapsulation efficiency, may migrate from the site of injection, and may exhibit undesirably rapid release of the drug. Particles that are "too large" may not easily pass through a syringe needle. Thus, the typical polydisperse particles generated by conventional fabrication techniques must be filtered or sieved to isolate particles within the desired size range, and the particles outside that range are wasted.

Moreover, with traditional technologies for spraying microdroplets from nozzle-type devices, the minimum particle size typically obtainable is limited by the size of the nozzle opening. Usually, it is not possible to make drops smaller than the nozzle opening; typically, droplet diameters are 1-4 times the diameter of the nozzle. This presents several difficulties as the desired particle size decreases. One problem is that fabrication of the nozzles themselves becomes more difficult as size decreases.

A second limitation stems from the pressure needed to pump fluids through small nozzles. The pressure required scales with $R^{-4}$, wherein R is the radius of the nozzle. Thus, pumping virtually any liquid through a nozzle of 5-μm diameter would require special equipment, if it could be done at all. Also, some compounds to be encapsulated, such as plasmid DNA, may be damaged by shear forces. In general, the damage is approximately inversely proportional to the diameter of the orifice. Thus, decreasing the nozzle diameter from 100 to 5 μm would increase the damage done to any encapsulated compound by a factor of 20.

Published U.S. Patent Application No. 2002/0,054,912 (published May 9, 2002, entitled "Microcapsules", to Kim et al.) hereby incorporated by reference, teaches a process wherein micro- and nano-sized particles, preferably spherical, are produced by pumping material, usually a polymer dissolved in an organic solvent, through a small orifice and then shaking the liquid with an acoustic type-wave, where the velocity of the fluid is increased beyond the velocity produced by pressure behind the liquid. In this process, the nozzle diameter may be larger than the particles produced. For example, 5-μm droplets can be prepared from a much larger nozzle, such as a nozzle of 100 μm diameter. The droplets are collected in a solution, and the presence of a surfactant prevents the droplets from sticking together before the evaporation of the organic solvent leads to the hardening of the droplets into microparticles.

The pressures needed to form very small particles are reduced to ranges easily obtained with commercial high-pressure pumps such as those commonly supplied with high-pressure liquid chromatography systems. Furthermore, the shear forces are greatly reduced for a given particle size, and the difficulties encountered with very small diameter nozzles are also eliminated. Aspects of the invention are described in "Fabrication of PLG microspheres with precisely controlled and monodisperse size distributions" J. Controlled Release 73(1):59-74 (May 18, 2001).

The vibration or shaking can be achieved by, for example, a piezoelectric transducer driven by a wave generator, and breaks the stream into a train of uniform droplets. Droplet size is determined by the orifice diameter, the solution flow rate, the vibration frequency and amplitude. Thus, by varying these four parameters droplet size can be controlled.

The velocity of the fluid is increased beyond the velocity produced by the pressure behind the liquid by employing an additional downward force that will 'pull' the liquid jet through the orifice, reducing the jet size below the diameter of the orifice. One example is an electrohydrodynamic technique in which electrical forces act to reduce the diameter of the liquid jet and the resulting droplets. The electrohydrodynamic technique is activated through injection of charge of desired polarity into the liquid by applying a high voltage either to the nozzle or directly into the liquid, for example, with a battery, or with a transformer and a rectifier to convert standard current. Outwardly directed electrical tension forces result at the charged liquid meniscus of the nozzle opening, enabling a smaller drop to fall from the nozzle (the "drip mode"). The reason for this reduction in drop size is believed to be that there are two forces present, gravitational and electrical, that are working together to pull the liquid off of the nozzle, while surface tension forces hold the liquid at the nozzle. As the amount of charge injected increases, the electrical tension forces accordingly increase, eventually dominating the gravitational and surface-tension forces and reducing the drop size. Further increase in charge injection beyond a certain threshold value results in very powerful electrical tension forces that literally pull the liquid out of the nozzle to form a thin charged liquid jet, which in turn breaks up into fairly uniform droplets (known as the "jet mode"). Jet mode changes from single-jet to multi-jet mode as charge injection is further increased.

Another example of an additional downward force employed is a separate liquid stream (typically immiscible) through the orifice, adjacent and parallel to the particle-forming liquid, at a velocity greater than the particle-forming liquid. The particle-forming liquid is pulled along by the drag forces at the liquid/liquid interface. The particle-forming jet is reduced in diameter by a factor that is proportional to the difference in linear velocities of the two streams.

BRIEF SUMMARY

In a first aspect, the present invention is a method of forming particles, comprising accelerating a first stream comprising a first liquid, applying a charging voltage of at most 1.5 kV to the first stream, and vibrating the first stream, to form particles.

In a second aspect, the present invention is a method of forming chitosan particles, comprising accelerating a first stream comprising an aqueous solution of chitosan, applying a charging voltage of at most 1.5 kV to the first stream, vibrating the first stream, to form particles; and maintaining the particles at a pressure of at least 0.1 mm Hg and of at most 760 mm Hg, while heating the particles to a temperature within ±50° C. of the boiling point of water at the pressure. The accelerating comprises contacting the first stream with a second stream, and the second stream comprises a hydrophobic liquid.

In a third aspect, the present invention is particles comprising chitosan having an average diameter of at least 50 µm to at most 100 µm. 90% of the particles have a diameter that is within 2% of an average diameter of the particles.

In a fourth aspect, the present invention is particles comprising chitosan having an average diameter of at least 1 µm to 50 µm. 90% of the particles have a diameter that is within 1 µm of an average diameter of the particles.

In a fifth aspect, the present invention is a method of forming gelatin particles, comprising accelerating a first stream comprising an aqueous solution of gelatin, applying a charging voltage of at most 1.5 kV to the first stream, and vibrating the first stream, to form particles.

BRIEF DESCRIPTION OF THE DRAWINGS

FIGS. 3 (A) and (B) are SEM micrographs of 60 µm chitosan microparticles.

FIGS. 4 (A) and (B) are SEM micrographs of cross-sections of 60 µm chitosan microparticles.

DETAILED DESCRIPTION

The technique described above is not best suited to the fabrication of chitosan particles. Chitosan dissolves in acidic water solution, and is thus delivered in aqueous droplets that are collected in a bath of an immiscible solvent. However, the presence of a surfactant does not separate the droplets as reverse micelles, and the chitosan droplets cluster before hardening into microparticles. The present invention provides a solution to this problem based on the discovery that charging the droplets prevents them from coalescing before hardening, thus providing a microparticle fabrication method especially suitable for hydrophilic polymers such as chitosan.

Figure 1:
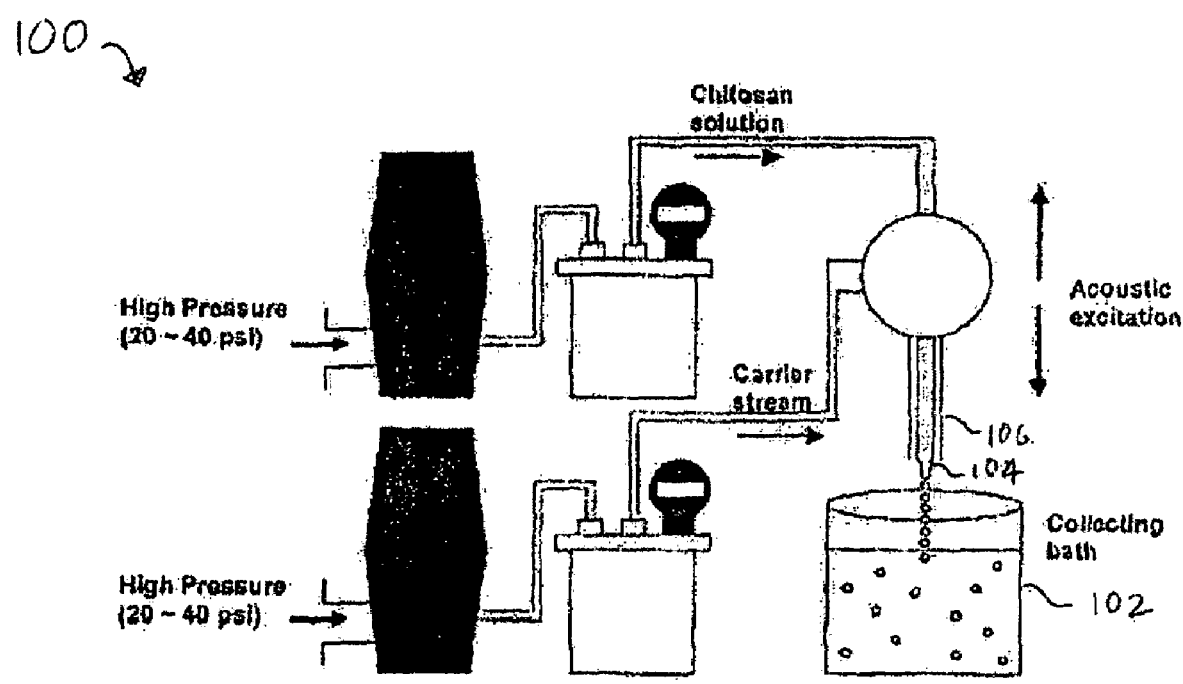
FIG. 1 is an illustration of an apparatus for fabricating the microparticles.

A chitosan solution is prepared by dissolving chitosan in an acidic aqueous solvent, and the solution is loaded in the apparatus 100 illustrated in FIG. 1. A water-immiscible solvent, such as a vegetable oil, is also loaded in the apparatus, and a collection bath 102 is loaded with an immiscible solvent. A stream of the chitosan solution is generated by an inner nozzle 104 and charged with a charging voltage, while a carrier stream of the immiscible solvent is generated by an outer nozzle 106 coaxial with the inner nozzle. The diameter of the inner nozzle is preferably greater than ½ of the average diameter of the particles, and more preferably at least equal to the average diameter of the particles. The carrier stream surrounds the inner stream of chitosan solution and flows through the outer nozzle with it. As described above, the carrier stream imposes frictional force on the inner chitosan stream to pull and accelerate it, and a liquid jet of chitosan solution thinner than the size of the inner nozzle orifice can be generated by adjusting the flow rate of the carrier stream. Acoustic excitation of a desired frequency is then applied to the stream, disrupting it to form a train of uniform droplets.

Further reduction in the droplet size can be achieved by placing a blade or a nanowire in front of a droplet exiting the nozzle so that the blade or the nanowire is placed in the flowing stream, thus chopping the droplet into two smaller droplets of equal or different sizes. When the two smaller droplets are of different size, the smaller of the two droplets can be made with a radius smaller than 5 µm, depending on the sharpness of the blade, the position of the blade, or the size of the nanowire The droplets are collected in the collection bath of an immiscible solvent, where the temperature of the bath is such as to induce evaporation of the aqueous solvent. The droplets do not aggregate due to the coulombic repulsion between their electric charges, and harden into chitosan microparticles. The microparticles are collected from the solvent, washed, dried and optionally treated with alkali to eliminate residual acidity from the chitosan solution.

The average diameter of the microparticles is at most 100 µm. More preferably, the average diameter of the microparticles is at most 50 µm. Yet more preferably, the average diameter of the microparticles is at least 1 µm and at most 50 µm. Most preferably, the average diameter of the particles is at least 10 nm and at most 50 µm. If the average diameter of the microparticles is at least 50 µm and at most 100 µl, 90% of the microparticles have a diameter that is within 2% of the average diameter of the microparticles. If the average diameter of the microparticles is at least 1 µm and at most 50 µm, 90% of the microparticles have a diameter that is within 1 µm of the average diameter of the microparticles.

The chitosan solution may be prepared by dissolving chitosan in an aqueous solvent containing one or more acids such as formic acid, acetic acid, propionic acid, trifluoroacetic acid, trichloroacetic acid, nitric acid, sulphuric acid, phosphoric acid, hydrofluoric acid, hydrochloric acid, hydrobromic acid, hydroiodic acid, perchloric acid and perbromic acid.

The applied charging voltage is preferably at least 0.5 kV and at most 1.5 kV, more preferably of at least 0.75 kV and at most 1.25 kV, and most preferably of at least 0.9 kV to at most 1.1 kV. Voltages such as those used in electrohydrodynamic droplet generating methods, generally in the 10 kV to 20 kV range, are likely to damage the pharmaceutical compositions contained in the droplets.

The solvent of the collection bath may contain one or more fluids immiscible with water, for instance synthetic or natural oils such as canola oil, corn oil, peanut oil, linseed oil, sunflower oil, soybean oil, flax oil, olive oil, grape-seed oil and coconut oil. The bath may also contain additional synthetic or natural excipients. The temperature of the bath is preferably from at least 90° C. to at most 170° C., more preferably from at least 110° C. to at most 150° C., and most preferably from at least 125° C. to at most 135° C. The evaporation may be conducted at lower temperatures by keeping the droplets at sub-atmospheric pressures, thus lowering the boiling point of the aqueous solvent. For instance, the evaporation may be conducted at a pressure of 0.54 atm, where the boiling point of water is at 84.4° C.

Where heat-driven evaporation of the aqueous solvent is not preferred, for instance in the preparation of gelatin microspheres, the collection bath is kept at temperatures in the 0 to 25° C., in order to promote spontaneous gelation of the aqueous solution. Optionally, a surfactant may be added to the aqueous solution or the collection bath.

After the hardening, the resulting microparticles are filtered, washed with a solvent such as ethanol to remove the oil, and optionally treated with a base to deprotonate their surface. A final washing in water may follow, after which the particles may be lyophilized. Also, the microparticles may be hardened by treatment with a crosslinking agent.

Chitosan microcapsules of controlled size and shell thickness may also be fabricated by inserting a coaxial nozzle inside the nozzle carrying the chitosan solution described above, yielding a stable, hollow jet of chitosan solution surrounding a coaxial jet of a gas or an immiscible liquid. A third, external carrier stream of an immiscible solvent as described above may be applied to the jet, obtaining multilayered droplets that are then hardened in the collection bath, yielding chitosan microcapsules containing the gas or the immiscible liquid.

The technique may also be applied for the fabrication of particles of hydrophilic polymers other than chitosan and gelatin, such as carboxy methyl cellulose, dextran, hydroxypropyl cellulose, poly(acrylamide), poly(acrylic acid), poly (allylamine) hydrochloride, poly(diallyldimethylammonium chloride), poly(N,N-dimethyl acrylamide), poly(ethylene glycol), poly(ethylene oxide), poly(maltotriose), poly(methacrylic acid), poly(N-isopropyl acrylamide), poly(propylene glycol), poly(styrene carboxylic acid), poly(styrene sulphonic acid), poly(styrene sulphonate), poly(vinyl acetate), poly(vinyl alcohol), poly(vinyl butyral), poly(2-vinyl-N-methylpyridinium iodide), poly(4-vinyl-N-methylpyridinium), poly(2-vinyl pyridine), poly(2-vinyl pyridinium bromide), poly(vinyl pyrrolidone), p(methyl vinyl ether), hydroxyalkyl starches such as hetastarch, alkylcellulose, hydroxyalkylcellulose, hydroxyarylcellulose, alginate, and copolymers thereof. Additionally, more than one polymer or copolymer may be used in order to obtain microparticles made of composite materials.

Additionally, the gelated microparticles may be treated with a cross-linking agent in order to modify, for instance, their mechanical properties and solubility. Examples of cross-linking agents include: aldehydes, such as glyceraldehyde, glutaraldehyde, dextran dialdehyde, and carbohydrates; diols, such as ethylene glycol, di(ethylene glycol), polyethylene glycol, propylene glycol, di(propylene) glycol, polypropylene glycol; unsaturated diesters such as ethylene glycol dimethacrylate, di(ethylene glycol) dimethacrylate, poly(ethylene glycol) dimethacrylate, poly(lauryl methacrylate-co-ethylene glycol dimethacrylate), propylene glycol dimethacrylate, di(propylene glycol) dimethacrylate, poly (propylene glycol) dimethacrylate; dihydrazides such as malonic dihydrazide, ethylmalonic dihydrazide, succinic dihydrazide, glutaric dihydrazide, adipic dihydrazide, isophthalic dihydrazide, oxalyl dihydrazide, pimelic dihydrazide, 3,3'-sulfonyldibenzenesulfonic dihydrazide; diisocyanates such as m-xylylene isocyanate, 4-methyl-m-phenylene diisocyanate, 2-methyl-m-phenylene diisocyanate, 3,3'-dimethoxy-4,4'-biphenylene diisocyanate, 4-Br-6-methyl-1,3-phenylene diisocyanate, 4-Cl-6-methyl-1,3-phenylene diisocyanate, toluene 2,4-diisocyanate, 1,3-phenylene diisocyanate, 1,4-phenylene diisocyanate, 2,4,6-trimethyl-1,3-phenylene diisocyanate, 1,4-diisocyanatebutane, 1,6-diisocyanatehexane, 1,8-diisocyanateoctane, isophorone diisocyanate; carbodiimides such as N,N-(3-dimethylaminopropyl)-N-ethyl carbodiimide (EDC); salts, such as $CaCl_2$; divinylsulfone, sulfonylurea, hydrolysable polyrotaxane, L-lysine methyl ester, and genipin. Cross-linking may also be carried out or aided by one or more enzymes.

The microparticles of the invention may include proteins and peptides such as human growth hormone, bovine growth hormone, erythropoietin, thrombopoietin, tissue plasminogen activator and derivatives, insulin, monoclonal antibodies (e.g., anti-human epidermal growth factor receptor2 (HERCEPTIN™), anti-CD20 (RITUXIMAB™), anti-CD 18, anti-vascular endothelial growth factor, anti-IgE, anti-CD 11a) and their derivatives, single-chain antibody fragments, human deoxyribonuclease I (DORNASE ALFA™, PULMOZYME™), type-1 interferon, granulocyte colony-stimulating factor, leutenizing hormone releasing hormone inhibitor peptides, leuprolide acetate, endostatin, angiostatin, porcine factor VIII clotting factor, interferon alfacon-1, pancrelipase (pancreatic enzymes) and the like.

Hormones and steroids (corticosteroids) useful for the practice of this invention include but are not limited to norethindrone acetate, ethinyl estradiol, progesterone, estrogen, testosterone, prednisone and the like.

Chemotherapeutics useful for the practice of this invention include but are not limited to taxol (PACLITAXEL™), vinblastine, cisplatin, carboplatin, tamoxifen and the like.

Non-steroidal anti-inflammatory drugs (NSAIDs) useful for the practice of this invention include but are not limited to piroxicam and the like.

Vaccine components useful for the practice of this invention include but are not limited to Hepatitis B, polio, measles, mumps, rubella, HIV, hepatitis A (e.g., HAVRIX™) and the like.

Analgesics useful for the practice of this invention include but are not limited to aspirin, acetaminophen, ibuprofen, naproxen sodium and the like.

Antibiotics useful for the practice of this invention include but are not limited to amoxicillin, penicillin, sulfa drugs, erythromycin, streptomycin, tetracycline, chlarithromycin, ciproflozacin, terconazole, azithromycin and the like.

Anti-depressants useful for the practice of this invention include but are not limited to ZOLOFT™, fluoxetine (PROZAC™), paroxetine (PAXIL™), citalopram, venlafaxine, fluvoxamine maleate, imipramine hydrochloride, lithium, nefazodone and the like.

Other biopharmaceutical compounds useful for the practice of the instant invention include but are not limited to sildenafil (VIAGRA™), acyclovir, gancyclovir, fexofenidine, celecoxib (CELEBREX™), rofecoxib (VIOXX™), androstenedione, chloroquine, diphenhydramine HCl, buspirone, doxazocin mesylate, loratadine, clomiphine, zinc gluconate, zinc acetate, hydrocortisone, warfarin, indinavir sulfate, lidocaine, novacaine, estradiol, norethindrone acetate, Medroxyprogesterone, dexfenfluramine, Dextroamphetamine, Doxycycline, thalidomide, fluticasone, fludarabine phosphate, etanercept, metformin hydrochloride, hyaluronate, tetrazocin hydrochloride, loperamide, ibogaine, clonazepam, ketamine, lamivudine (3TC™), isotretinoin, nicotine, mefloquine, levofloxacin, atorvastatin (LIPITOR™), miconazole nitrate (MONISTAT™), ritonavir, famotidine, simvastatin (ZOCOR™), sibutramine HCl monohydride, ofloxacin, lansoprozole, raloxifene (EVISTA™), zanamivir (RELENZA™), oseltamivir phosphate, 4-phenylbutyric acid sodium salt, chlorpromazine, nevirapine, zidovudine, cetirizine hydrochloride (ZYRTEC™), bisphosphonates such as pamidronate and zoledronate, nifedipine, felodipine, and the like.

Materials which can further be utilized for the practice of this invention can be found in *Physician's Desk Reference* 2000, 54th Edition, ISBN: 1563633302, *AHFS* 99 *Drug Information*, Amer. Soc. of Health System, ISBN: 1879907917 and U.S. Pat. No. 5,019,400 all incorporated herein by reference in their entirety.

The microparticles of the present invention may be used to incorporate other materials, such as salts, metals, sugars, surface active agents, acids, bases, stabilizers and release enhancing agents. In general, these and other materials (such as polymers, biopharmaceutical compounds and other ingredients) may be incorporated into the outer shell, into the core, in each shell individually or at various levels of the concentric shells. Heterogenous mixture of chitosan and pharmaceutical compounds may also be included.

The microparticles of the invention may be used for many biomedical applications, such as the following:

Passive targeting of phagocytosis. Cells of the immune system, especially macrophages and dendrocytes, are targets for immunization. These "professional" antigen-presenting cells (APCs) can elicit a desired T-cell response to vaccine components. APCs are typically capable of phagocytosis of particles in the range of 1 to 10 μm; most other types of cells in the body cannot internalize such large particles. By generating in this size range particles containing vaccine components, one can passively target delivery of the vaccine to APCs. Current technologies allow formation of particles of this size, but only with significantly broad size distributions. This methodology allows generation of vaccine-encapsulating chitosan microparticles in which essentially 100% of the particles are of the desired size. APC targeting can be optimized with no waste of expensive vaccine components in microparticles that are too large or too small.

Capillary embolization. Blood vessel size varies throughout the body with the smallest vessels being the capillaries. Tumor tissues typically exhibit particularly tortuous capillary beds that feed the rapidly growing cancer cells. One approach to targeting tumor tissues is to deliver a therapeutic encapsulated in microparticles of a size such that they can become lodged in narrow capillaries. The microparticles are then injected into an artery feeding the tumor. Particles which are too large will become lodged in larger vessels and the therapeutic may be blocked from reaching all of the tumor. Particles which are too small will pass through the tumor and could deliver the therapeutic to other healthy tissue; a serious problem since many anti-cancer agents are, of course, cytotoxic. The availability of microparticles of a precise size will allow the maximization of the number of particles lodged in the smallest capillaries and, therefore, the amount of therapeutic delivered to the desired location.

Targeting by nano-particles. Biodegradable polymer particles less than 1 μm in diameter (nano-particles or nanocapsules) have several specific applications in drug delivery. For example, particles less than 150 nm in diameter can be targeted for receptor-mediated endocytosis by many different types of cells. Nanoparticles are also useful for oral administration wherein the particles can traverse the intestinal epithelium and be taken up by the M-cells and Peyer's patches. Particles that are too large are poorly taken up, particles that are too small contain little therapeutic. Most current methods for biodegradable polymer nanoparticle fabrication, of which there are many, result in wide variations in particle size. For example, phase inversion nanoencapsulation, in which polymer and drug are dissolved in a solvent (e.g., methylene chloride) and subsequently poured into a non-solvent phase (e.g., petroleum ether), yields particles ranging from 100 to 5000 nm. In contrast, the controlled size distribution will allow optimal nanoparticle targeting.

Control of drug release rate from solid microparticles. Many controlled-release drug delivery systems include microparticles formed from biodegradable polymers. Therapeutic compounds encapsulated in the microparticles are released as the polymer erodes, most often by hydrolysis, in the aqueous environment within the body. The drag release rate depends on several factors such as polymer composition, polymer molecular weight, microparticle porosity, etc. An especially critical parameter is particle size. In general, smaller particles with larger surface and surface-to-volume ratio erode and release therapeutic compounds more quickly than larger particles.

The ability to precisely control microparticle size distribution allows for unprecedented control over drug release rates. By varying liquid flow rate, vibration frequency and amplitude, and charging potential, particle size can be controlled. Furthermore, by continuously and smoothly varying such parameters, pre-defined size distributions can be generated. Since drug release rate depends on particle size distribution, an appropriate size distribution that will provide a desired release rate profile (e.g., zero-order release, pulsatile release, etc.) can then be determined.

Fabrication of composite core/shell microparticles. With the multi-nozzle methodology, composite particles of two or more different materials can be fabricated. Fine control of shell thickness and particle diameter are possible. The two phases may comprise: a gas core within a chitosan shell; a drug-containing aqueous core within a chitosan shell (the shell could also encapsulate a second or the same compound); a polymer core encapsulating a drug compound within a polymer shell (wherein either the core or the shell may be of chitosan) encapsulating a second or the same compound. Such particles could produce novel and useful drug-release rate profiles.

Fabrication of nanoshells. Virtually any compound can be encapsulated in the interior phase of the particle. If DNA (or other nucleic acids) are encapsulated, "artificial virus" particles that may be particularly useful for gene delivery can be produced.

Pharmaceutical compounds which can be encapsulated/released by the instant invention include but are not limited to nucleic acids, proteins and peptides, hormones and steroids, chemotherapeutics, NSAIDs, vaccine components, analgesics, antibiotics, anti-depressants, and the like.

Nucleic acids useful for the practice of this invention include but are not limited to DNA, RNA, peptide-nucleic acids, oligonucleotides, modified to improve stability (e.g., phosphorothioates, aminophosphonates or methylphosphonates).

EXAMPLES

(1) Uniform Chitosan Particle Fabrication

A 1% (w/v) chitosan solution was prepared by adding 1 gr of chitosan to 100 mL of 0.2 M aqueous acetic acid and stirring for 3~4 hours. The solution was filtered through a glass filter and supplied to the main stream tank of the system.

Canola oil was used for the carrier stream and the collection bath. The oil was heated to ~130° C. and supplied to the carrier stream tank and the collection bath. The carrier stream tank and the collection bath were placed on stirrer hot plates to maintain the oil at a temperature>100° C. while the chitosan solution drops were being generated.

A single nozzle was used to fabricate the solid particles. A high-pressure syringe pump was used to generate the chitosan solution main stream with a flow rate resolution of 1 µL/hr. The carrier stream was pressurized in a container at 30 psi and its flow rate was regulated with a micro-valve in the flow line.

A stable jet with a desired main stream diameter was obtained by applying the appropriate main stream and carrier stream flow rate, and acoustic excitation was applied to the jet. The jet was disrupted into droplets of a size that could be controlled by changing the frequency of the acoustic excitation or the flow rates of the main and carrier stream, respectively.

While the droplets were being generated, a charging voltage of 1 kV was applied, yielding droplets of the same polarity that spread in a canola oil collection bath. The temperature of the collection bath was maintained above 100° C., and the drops hardened through solvent evaporation while staying separated due to coulombic repulsion. The resulting microparticles were left in the collection bath for a total of 1~2 hours. The collection bath containing the chitosan particles was then stirred on a stirrer hot plate for 3~4 hours to bring water evaporation to completion.

The microparticles were filtered from the oil bath and rinsed with ethanol. Washing in 1 M aqueous sodium hydroxide solution followed in order to de-protonate the surface of the microparticles so that they would not dissolve in water. The particles were then washed with water several times, suspended in water, centrifuged and lyophilized for 2 days.

Figure 2:
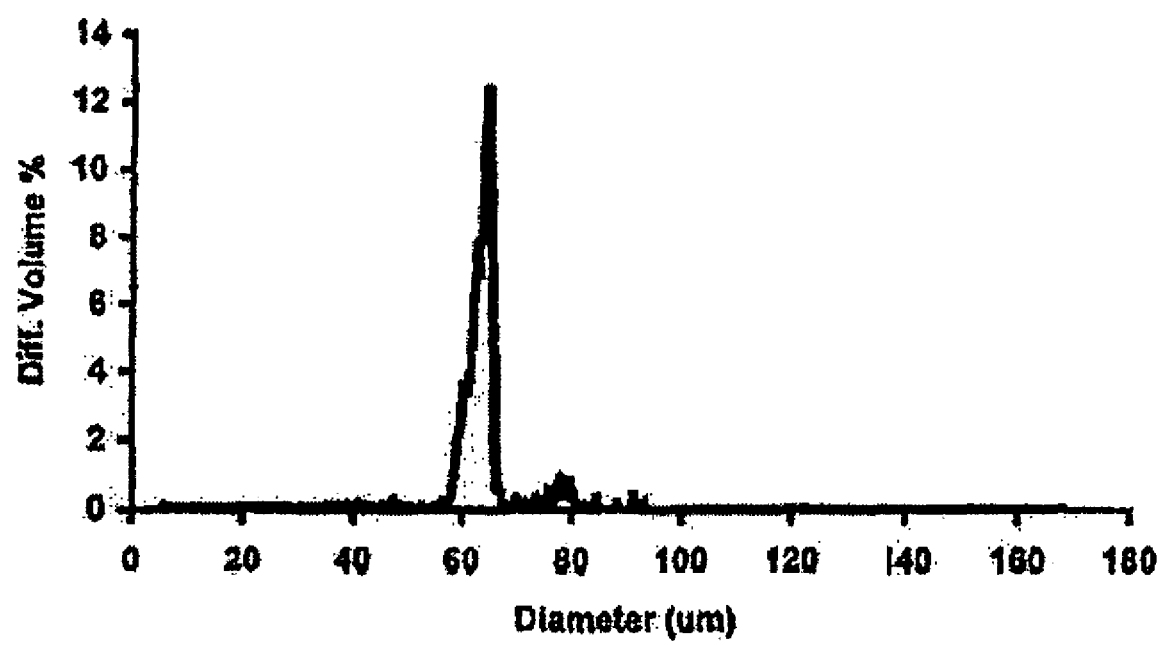
FIG. 2 is a graph of the size distribution of a batch of 60 µm chitosan microparticles.

FIG. 2 illustrates the size distribution as determined by a Coulter Multisizer. The SEM micrographs of FIG. 3 show the uniform size distribution of 60 µm chitosan particles obtained with the method of the invention, whereas the SEM micrographs of FIG. 4 illustrate their high density and homogeneous morphology.

(2) Uniform Alginate Particle Fabrication

The above method used for fabricating chitosan microparticles was also used for fabricating alginate microparticles, except sodium alginate dissolved in water was used instead of the chitosan solution.

The microparticles were cross-linked in 0.1 M CaCl$_2$ aqueous solution at room temperature for 2 days followed by filtering and repeated washing in deionized water. The particles were then suspended in water, centrifuged and lyophilized for 2 days. Aldehydes may also be used as cross-linking agents.

(3) Uniform Crosslinked Gelatin Microparticle Fabrication

A gelatin solution was obtained by dissolving 1 g of gelatin in 20 mL of deionized water at 40° C. The solution was supplied to the main stream tank of the system described in Example 1. Canola oil was used for the carrier stream and the collection bath. The carrier stream solution was maintained at room temperature, whereas the collection bath was kept at 0 to 4° C.

A stable jet with a desired main stream diameter was obtained by applying the appropriate flow rates of the main stream and carrier stream, and the jet was broken into droplets by acoustic excitation.

While the droplets were being generated, a charging voltage of 0.5 to 1 kV was applied, yielding charged droplets that spread in the collection bath. The temperature of the collection bath was maintained at 0 to 4° C., and the droplets were gelled before aggregation.

Figure 5:
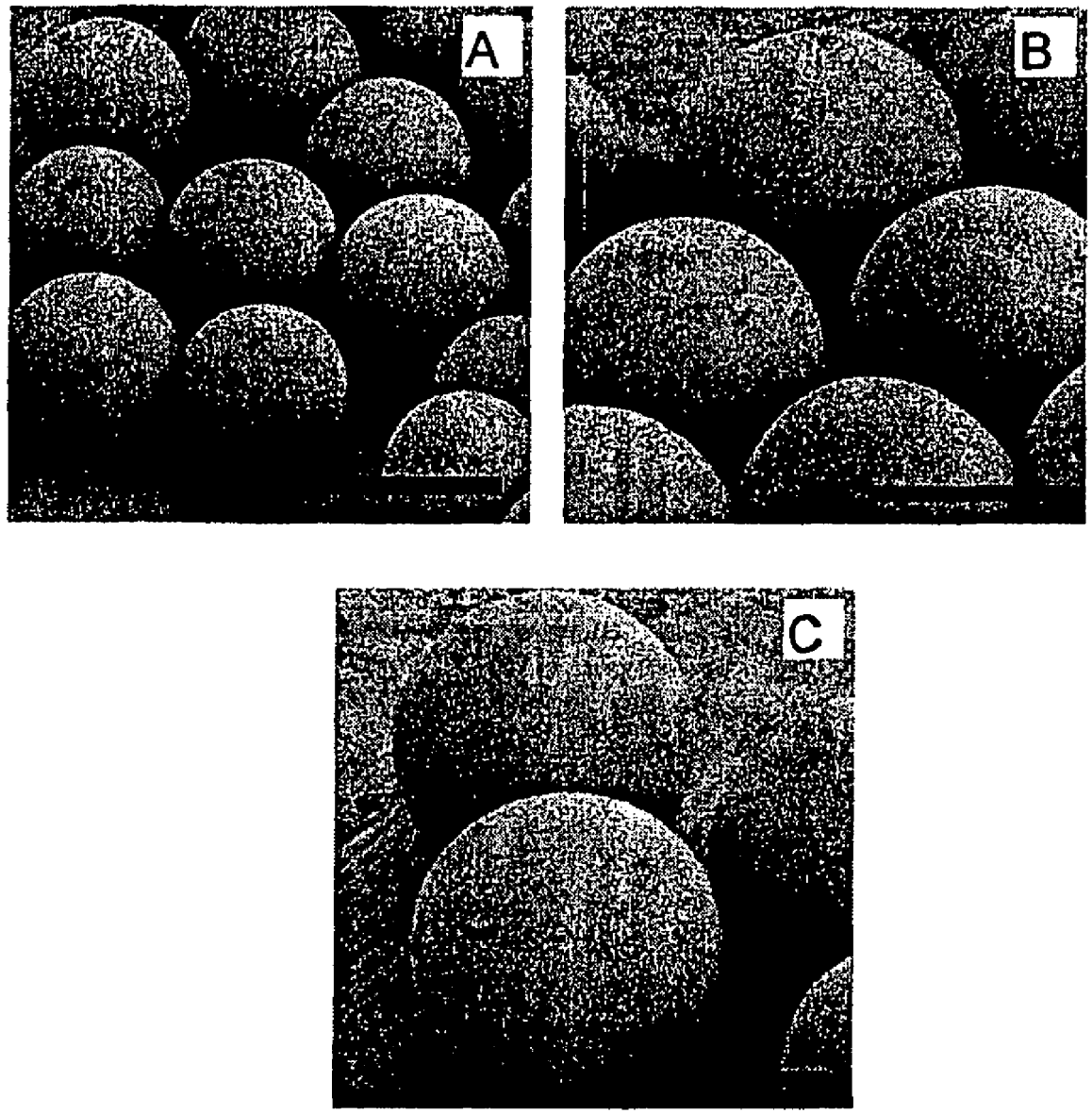
FIG. 5 is SEM micrographs of gelatin microspheres of isoelectric pH=5.0 prior to crosslinking. The scale bar=20 µm. The diameter of the microspheres are (A) 15 µm. (B) 30 µm. (C) 45 µm.
Figure 6:
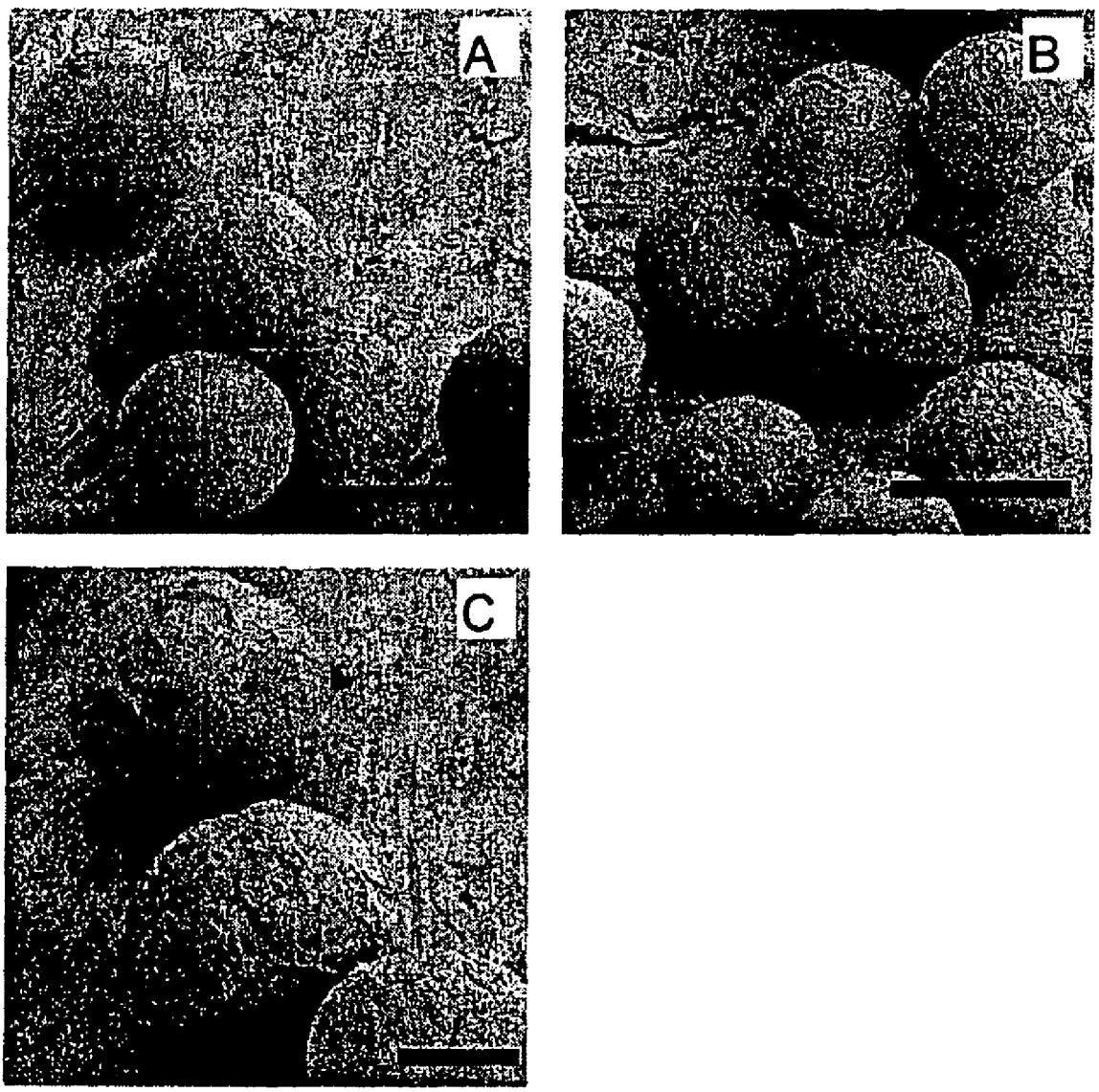
FIG. 6 is SEM micrographs of gelatin microspheres of isoelectric pH=9.0 prior to crosslinking. The scale bar=20 µm. The diameter of the microspheres are (A) 15 µm. (B) 20 µm. (C) 45 µm.

The collection bath containing the gelatin gel particles was then stirred slowly for 1 hr while maintaining the low temperature. The same amount of cold acetone as that of the oil was added to the collection bath and the resulting mixture was stirred for 30 min to extract water in gelatin hydrogel drops. The uniform gelatin microspheres were then filtered, washed with cold acetone several times and lyophilized for 2 days. FIG. 5 illustrates the uniform size distribution of gelatin microparticles with an isoelectric pH of 5.0. FIG. 6 illustrates the uniform size distribution of gelatin microparticles with an isoelectric pH of 9.0.

20 mL of 0.1% solution of the surfactant TWEEN 80™ (Uniqema, New Castle, Del.) was prepared and 500 µL of glutaraldehyde was added to the solution. The pH of the solution was adjusted depending on the isoelectric pH of the gelatin. The solution was then stored at 0 to 4° C. After lyophilization, 20 mg of uniform gelatin microspheres were suspended in the prepared glutraldehyde solution and cured for 24 hr at 0 to 4° C. with stirring.

Figure 7:
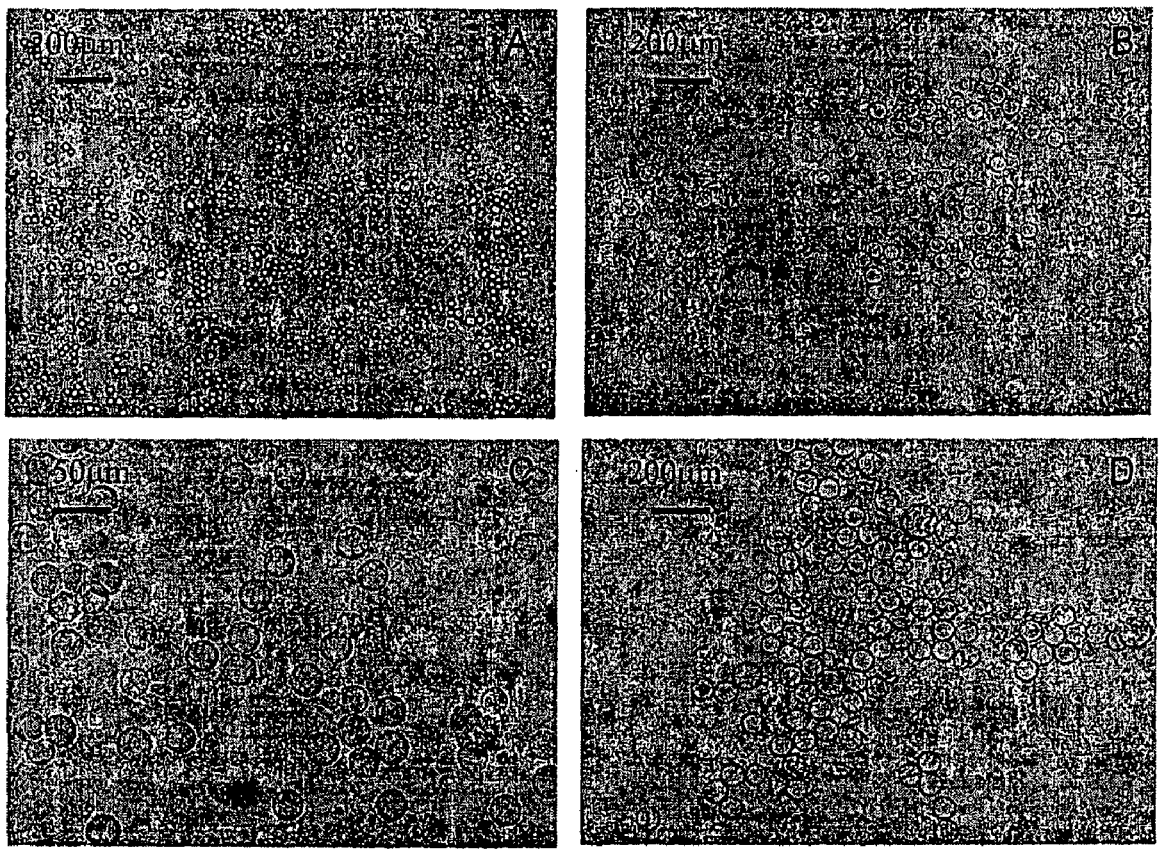
FIG. 7 is light micrographs of gelatin microspheres after crosslinking. Initial diameter of microspheres after swelling in aqueous media: (A) 50 µm (10×). (B) 50 µm (40×). (C) 100 µm (10×). (D) 150 µm (10×).
Figure 8:
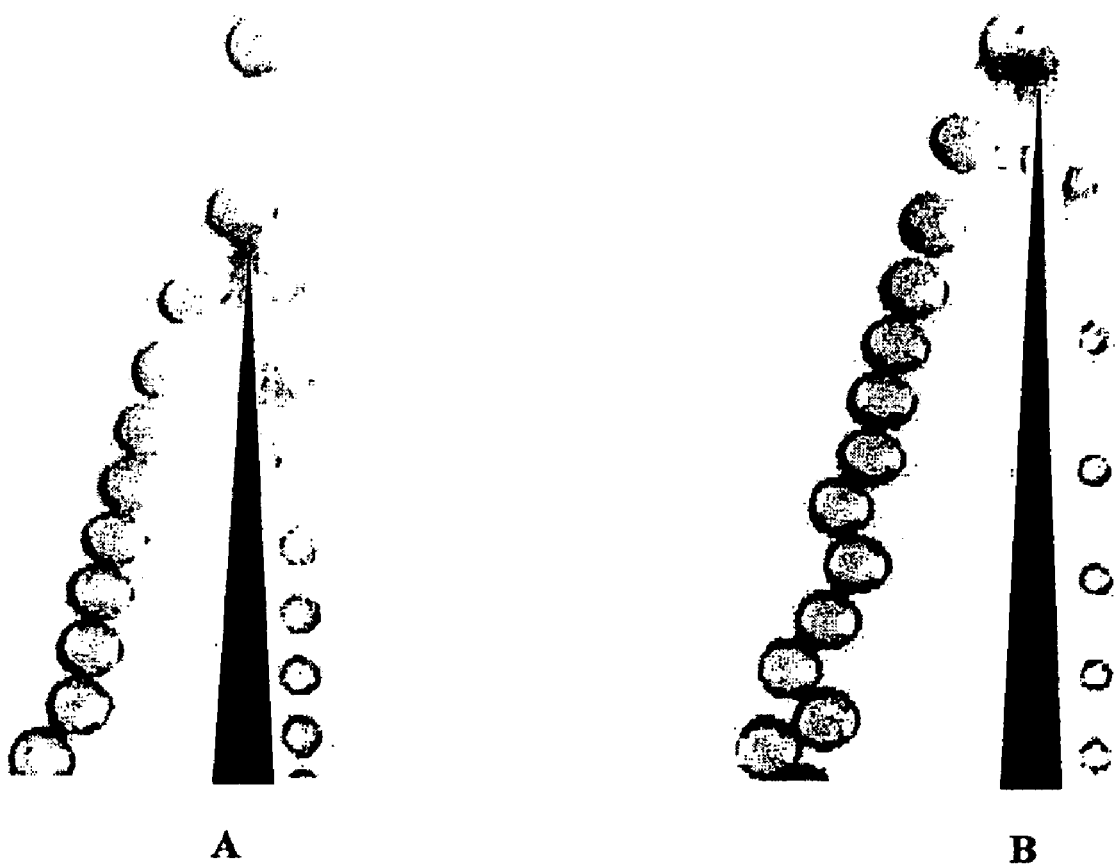
FIG. 8 illustrates a blade chopping 150 µm droplets into smaller droplets of: (A) 142-µm-diameter and 80-µm-diameter. (B) 149-µm-diameter and 40-µm-diameter.

After crosslinking, the microspheres were filtered and washed thoroughly with deionized water. The microspheres were then suspended in 100 mM glycine solution and stirred at room temperature for 1 hr. The microspheres were filtered once more, washed thoroughly with deionized water and lyophilized. FIG. 7 illustrates light micrographs of crosslinked microsphere. The particles of panels A and B had an original, pre-crosslinking diameter of 50 µm. The particles of panel C had an original diameter of 100 µm, whereas the particles of panel D had an original diameter of 150 µm.

(4) Droplet Chopping with Blades

A solution of ethyl cellulose and red rhodamine dye dissolved in methylene chloride was broken into 150-µm-diameter droplets via the acoustic and carrier stream method described above. The droplets were then chopped into droplets of two different sizes with a blade, where the two different sizes depended on the position of the blade tip, as shown by the black arrow. FIG. (8A) illustrates the chopping of droplets into smaller droplets of respectively 142-µm-diameter and 80-µm-diameter. FIG. (8B) illustrates the chopping of the droplets into smaller droplets of respectively 149-µm-diameter and 40-µm-diameter.

The invention claimed is:

1. A method of forming particles, comprising:
accelerating a first stream comprising a first liquid with a carrier stream that imposes frictional force on the first stream to accelerate the first stream;

applying a charging voltage to the first stream;
vibrating the first stream, to form particles; and
separating the particles into sub-particles with a device in-line with a flow of the particles, wherein the device comprises a blade or a nanowire.

2. The method of claim 1, further comprising solidifying the particles.

3. The method of claim 1, wherein the first liquid comprises a hydrophilic polymer.

4. The method of claim 3, wherein the first liquid comprises one or more polymers selected from the group consisting of chitosan, gelatin, alginate, carboxy methyl cellulose, dextran, hydroxypropyl cellulose, poly(acrylamide), poly(acrylic acid), poly(allylamine) hydrochloride, poly(diallyldimethylammonium chloride), poly(N,Ndimethyl acrylamide), poly(ethylene glycol), poly(ethylene oxide), poly(maltotriose), poly(methacrylic acid), poly(N-isopropyl acrylamide), poly(propylene glycol), poly(styrene carboxylic acid), poly(styrene sulphonic acid), poly(styrene sulphonate), poly(vinyl acetate), poly(vinyl alcohol), poly(vinyl butyral), poly(2-vinyl-N-methylpyridinium iodide), poly(4-vinyl-N-methyl pyridinium), poly(2-vinyl pyridine), poly(2-vinyl pyridinium bromide), poly(vinyl pyrrolidone), p(methyl vinyl ether), hydroxyalkyl starch, alkylcellulose, hydroxyalkylcellulose, hydroxyarylcellulose, and copolymers thereof.

5. The method of claim 3, wherein the particles comprise a pharmaceutical composition.

6. The method of claim 3, wherein the particles comprise a core and a shell.

7. The method of claim 6, wherein the particles comprise a plurality of shells.

8. The method of claim 7, wherein the core comprises a pharmaceutical composition.

9. The method of claim 3, wherein the carrier stream is a second stream.

10. The method of claim 9, wherein the second stream surrounds the first stream.

11. The method of claim 1, further comprising forming the first stream by passing the first liquid through a nozzle.

12. The method of claim 11, wherein the nozzle has a diameter greater than ½ of an average diameter of the particles.

13. The method of claim 11, wherein the nozzle has a diameter at least equal to an average diameter of the particles.

14. The method of claim 3, wherein the particles have an average diameter of at least 10 nm to at most 100 um.

15. The method of claim 1, wherein the particles have an average diameter of at least 50 um to at most 100 um, and 90% of the particles have a diameter that is within 2% of an average diameter of the particles.

16. The method of claim 1, wherein the particles have an average diameter of at least 1 um to at most 50 um, and 90% of the particles have a diameter that is within 1 um of an average diameter of the particles.

17. The method of claim 1, further comprising passing the first liquid through a nozzle comprising the device.

18. A method of forming chitosan or alginate particles, comprising:
accelerating a first stream comprising a solution of chitosan or alginate with a second stream that imposes frictional force on the first stream;
applying a charging voltage to the first stream;
vibrating the first stream, to form particles;
separating the particles into sub-particles with a device in-line with a flow of the particles, wherein the device comprises a blade or a nanowire; and
maintaining the sub-particles at a pressure of at least 0.1 mm Hg and of at most 760 mm Hg, while heating the sub-particles to a temperature within ±50° C. of the boiling point of water at the pressure;
wherein the accelerating comprises contacting the first stream with the second stream, and the second stream comprises a hydrophobic liquid.

19. The method of claim 18, wherein particles comprising chitosan or alginate have an average diameter of at least 1 um to at most 100 um, wherein 90% of the particles have a diameter that is within 1 um of an average diameter of the particles.

20. A method of forming gelatin particles, comprising:
accelerating a first stream with a second stream,
applying a charging voltage to the first stream;
vibrating the first stream, to form particles;
separating the particles into sub-particles with a device in-line with a flow of the particles, wherein the device comprises a blade or a nanowire, and wherein the accelerating comprises contacting the first stream with the second stream.

21. The method of claim 1, wherein the device is a nanowire.

22. The method of claim 1, wherein the device is a blade.

23. The method of claim 1, wherein the sub-particles are of substantially equal size based on a position of a tip of the device.

24. The method of claim 1, wherein the sub-particles are of different size based on a position of a tip of the device.

25. The method of claim 18, wherein the device is a nanowire.

26. The method of claim 18, wherein the device is a blade.

27. The method of claim 18, wherein the sub-particles are of substantially equal size based on a position of a tip of the device.

28. The method of claim 18, wherein the sub-particles are of different size based on a position of a tip of the device.

29. The method of claim 20, wherein the device is a nanowire.

30. The method of claim 20, wherein the device is a blade.

31. The method of claim 20, wherein the sub-particles are of substantially equal size based on a position of a tip of the device.

32. The method of claim 20, wherein the sub-particles are of different size based on a position of a tip of the device.

* * * * *